United States Patent [19]

Giraudon

[11] 4,259,506
[45] Mar. 31, 1981

[54] NEW 3-UREIDO-(THIO)-CHROMONE DERIVATIVES

[75] Inventor: Raymond Giraudon, Lesigny, France

[73] Assignee: Philagro, Lyons, France

[21] Appl. No.: 967,098

[22] Filed: Dec. 7, 1978

[30] Foreign Application Priority Data

Dec. 12, 1977 [FR] France ............................... 77 38152

[51] Int. Cl.³ .................. C07D 311/22; C07D 335/06
[52] U.S. Cl. ......................................... 549/23; 71/81;
71/91; 260/345.2; 548/218
[58] Field of Search .................... 260/327 TH, 345.2;
71/81, 91, 118, 119; 549/23

[56] References Cited

U.S. PATENT DOCUMENTS 2,624,664  1/1953  Mowry et al. .......................... 71/91
3,856,501  12/1974  Zech et al. ............................... 71/91

FOREIGN PATENT DOCUMENTS 2259589  8/1976  France .................................. 260/345.2

OTHER PUBLICATIONS

Eisert et al., Chem. Ber., vol. 109, pp. 3462 to 3472, (1976).
Sarda et al., Chem. Abstracts, vol. 86, abst. No. 5270y, (1977).

*Primary Examiner*—John D. Randolph
*Attorney, Agent, or Firm*—Robert E. Burns; Emmanuel J. Lobato; Bruce L. Adams

[57] ABSTRACT

They correspond to the formula:

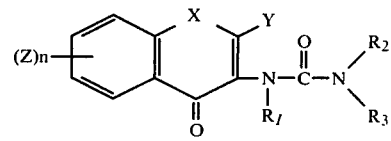

in which: X is an oxygen or sulphur atom, Y is a hydrogen atom or an alkyl radical ($C_1$-$C_4$), Z is a halogen atom or an alkyl ($C_1$-$C_6$), cycloalkyl ($C_5$-$C_7$), alkoxy ($C_1$-$C_4$) or phenyl radical, n is a number equal to 0, 1, 2 or 3, $R_1$ is a hydrogen atom or an alkyl radical ($C_1$-$C_4$) and $R_2$ and $R_3$, which are identical or different, each represent a hydrogen atom or an alkyl ($C_1$-$C_6$), alkenyl ($C_2$-$C_4$) or alkynyl ($C_2$-$C_4$) radical, or together form a heterocyclic ring possessing from 5 to 6 ring members and optionally containing, in addition to the nitrogen atom, an oxygen or sulphur atom as a hetero-atom.

These compounds can be used for selectively destroying weeds in crops such as maize, soya, cotton, sunflower, rice and horse bean.

7 Claims, No Drawings

NEW 3-UREIDO-(THIO)-CHROMONE DERIVATIVES

The present invention relates to new 3-ureido(thio)-chromone derivatives and to the preparation of these compounds. It also relates to herbicidal compositions in which at least one of these derivatives is present as the active ingredient, and to the treatments for selectively destroying weeds, which are carried out using these compositions.

The compounds according to the invention correspond to the general formula:

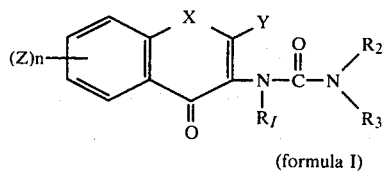

(formula I)

in which:
X represents an oxygen or sulphur atom.
Y represents a hydrogen atom or an alkyl radical containing from 1 to 4 carbon atoms.
Z represents a halogen or an alkyl radical containing from 1 to 6 carbon atoms, a cycloalkyl radical containing from 5 to 7 carbon atoms, an alkoxy radical containing from 1 to 4 carbon atoms, or a phenyl radical.
n is an integer equal to 0, 1, 2 or 3. If n is equal to 2 or 3, the substituents Z can be identical or different.
$R_1$ represents a hydrogen atom or an alkyl radical containing from 1 to 4 carbon atoms.
$R_2$ and $R_3$, which are identical or different, each represent a hydrogen atom or an alkyl radical containing from 1 to 6 carbon atoms, an alkoxy radical containing from 1 to 6 carbon atoms, an alkenyl radical containing from 2 to 4 carbon atoms or an alkynyl radical containing from 2 to 4 carbon atoms, or form, together with the nitrogen atom to which they are bonded, a heterocyclic ring possessing from 5 to 6 ring members and optionally containing, in addition to the nitrogen atom, a second hetero-atom chosen from oxygen and sulphur atoms.

The invention preferably relates to the compounds according to the formula I in which: X represents an oxygen or sulphur atom, Y represents a hydrogen atom, n is equal to 0 or 1, Z represents an alkyl radical containing from 1 to 6 carbon atoms, or a halogen atom, $R_1$ has the same meaning as in the formula I and $R_2$ and $R_3$, which are identical or different, each represent a hydrogen atom or an alkyl radical containing from 1 to 4 carbon atoms.

Some chromone derivatives have already been described in the literature. Thus, U.S. Pat. No. 3,906,005 describes optionally substituted 3-nitrochromones which possess anti-fungal properties and can be used more particularly for the treatment of skin diseases.

Furthermore, French Patent Application No. 2,259,589 claims N-carbonylated derivatives of 2-aminochromones, including 2-ureidochromone derivatives, and indicates that these compounds possess remarkable analgesic, anti-inflammatory and cardio-stimulant properties and that they can be used as medicaments. The compounds according to the invention are clearly different from those claimed in the two above-mentioned documents. Furthermore, they exhibit an excellent herbicidal activity and their use is therefore very different from that of the compounds claimed in these two documents.

The compounds according to the invention can be prepared in accordance with the following processes:

PROCESS A

The compounds of the general formula:

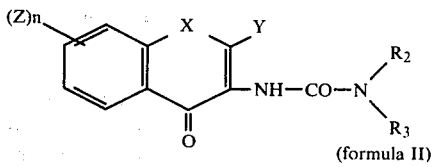

(formula II)

in which X, Y, Z, n, $R_2$ and $R_3$ have the same meaning as in the formula I, can be obtained in accordance with the process comprising the following stages:

1. The action of phosgene on an amino-(thio)-chromone of the formula:

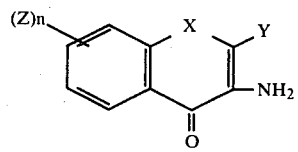

in which X, Y, Z and n have the same meaning as in the formula I, the reaction being carried out at a temperature between about 50° and 120° C. in an inert organic solvent medium like an aromatic hydrocarbon such as e.g. toluene.

Depending on whether the starting compound is an aminochromone (X=O) or an aminothiochromone (X=S), the relevant equation is respectively the first or second of the equations described below:

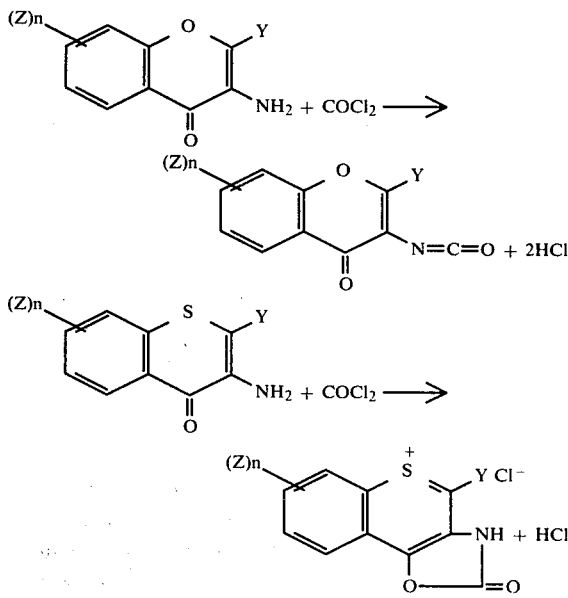

in which Y, Z and n have the same meaning as in the formula I.

2. The action of a compound of the formula

in which $R_2$ and $R_3$ have the same meaning as in the formula I, on the compound resulting from the preceding stage.

The reaction is carried out at a temperature between about 20° and 120° C. in an anhydrous inert organic solvent medium like an aromatic hydrocarbon such as e.g. toluene.

In the case of the compounds in which X represents an oxygen atom, it is preferred to use approximately equimolecular amounts of the compound of the formula

and of the 3-isocyanatochromone resulting from the first stage.

In the case of the compounds in which X represents a sulphur atom, a molar excess of the compound of the formula

is used, relative to the compound resulting from Stage 1. Preferably, at least two molar equivalents of the compound of the formula

are used per molar equivalent of the compound resulting from the first stage.

PROCESS B

The compounds of the general formula:

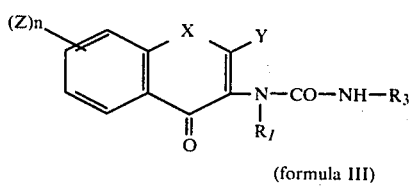

(formula III)

in which X, Y, Z, n and $R_1$ have the same meaning as in the formula I and $R_3$ represents an alkyl radical containing from 1 to 6 carbon atoms an alkoxy radical containing from 1 to 6 carbon atoms or an alkenyl or alkynyl radical containing from 2 to 4 carbon atoms, can be obtained by reacting an isocyanate of the formula OC-N—$R_3$, in which $R_3$ has the same meaning as above, with a compound of the formula:

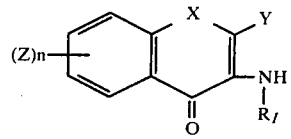

(formula IV)

in which X, Y, Z, n and $R_1$ have the same meaning as in the formula I.

The reaction is carried out in an anhydrous inert organic solvent medium like an aromatic hydrocarbon such as e.g. toluene, at a temperature between about 20° and 150° C. and optionally under pressure.

PROCESS C

The compounds of the general formula:

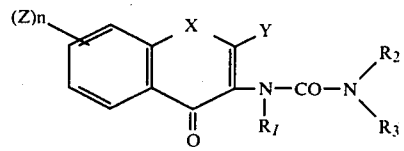

(formula V)

in which X, Y, Z, n, $R_1$, $R_2$ and $R_3$ have the same meaning as in the formula I, can be obtained in accordance with the process comprising the following successive stages:

1. The action of phosgene on triethylamine to give the phosgene/triethylamine complex.

The reaction is carried out in an inert organic solvent medium like an aromatic hydrocarbon such as e.g. toluene, at a temperature between about 0° and 20° C. and preferably below 5° C.

2. The action of the complex resulting from the preceding stage on a compound of the formula:

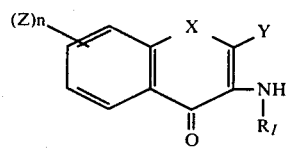

in which X, Y, Z, n and $R_1$ have the same meaning as in the formula I, in order to give the compound of the formula:

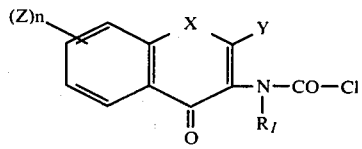

The reaction is carried out at a temperature between about 0° and 20° C. in an inert organic solvent medium such as an aromatic hydrocarbon, e.g. toluene.

3. The action of the compound resulting from the preceding stage on a compound of the formula

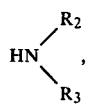

in which $R_2$ and $R_3$ have the same meaning as in the formula I.

The reaction is carried out at a temperature between about 0° and 20° C. in an inert organic solvent medium such as an aromatic hydrocarbon.

This process C makes it possible, in particular, to prepare the compounds according to the formula I in which $R_1$, $R_2$ and $R_3$ do not represent a hydrogen atom.

The substituted 3-amino-(thio)-chromones according to the formula IV, which can be used as the starting material in the case of the processes A, B and C described above, can be prepared in accordance with the following processes:

PROCESS 1

The compounds according to the formula IV in which X represents an oxygen atom and $R_1$ represents a hydrogen atom can be obtained by reducing the corresponding 3-nitrochromones in accordance with the method described in Tetrahedron Letters No. 9, pages 719-20 (1976), in the case of the preparation of 3-aminochromone. This method is also described in U.S. Pat. No. 3,906,005.

PROCESS 2

The compounds according to the formula IV in which Y and $R_1$ represent a hydrogen atom can be obtained by catalytically hydrogenating the corresponding 2-halogeno-3-amino-(thio)-chromones, the preparation of which is described in Chem. Ber., 109, pages 3,462-3,472 (1976).

PROCESS 3

The compounds according to the formula IV in which Y and $R_1$ represent a hydrogen atom can also be prepared by heating an optionally substituted 3-acetamido-(thio)-chromone in methanol in the presence of hydrochloric acid, the 3-acetamido-(thio)-chromone itself being obtained by heating an optionally substituted 3-acetamido-(thio)-chroman-4-one in the presence of triphenylmethanol and trifluoroacetic acid. The starting 3-acetamido-(thio)-chromanone is prepared in accordance with the process described in Evr. J. Med. Chem. Chim. Ther., II (2), pages 145-54, 1976, in the case of 3-acetamidochroman-4-one.

PROCESS 4

The compounds according to the formula IV in which X represents a sulphur atom, $R_1$ represents a hydrogen atom and Y represents an alkyl radical can be obtained by treating the corresponding 2-alkylthiochromanone with isoamyl nitrite and reducing the oxime, thus obtained, by catalytic hydrogenation.

PROCESS 5

The compounds according to the formula IV in which $R_1$ represents an alkyl radical can be obtained in accordance with a process comprising the following stages:

a. The action of a compound of the formula

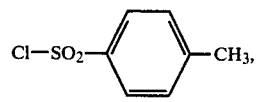

in the presence of pyridine, on an amino-(thio)-chromone of the formula:

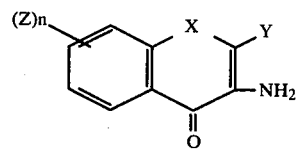

in order to give a compound of the formula:

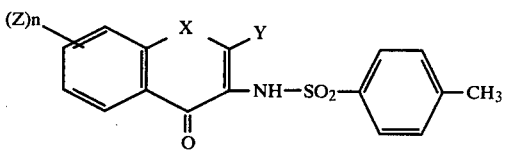

in accordance with the method described in Houben Weyl, Methoden der Organischen Chemie (Methods of Organic Chemistry), Volume 9, page 611.

b. The action of an iodide of the formula $IR_1$ on the compound resulting from the preceding stage, in the presence of alkaline agent, in order to give a compound of the formula:

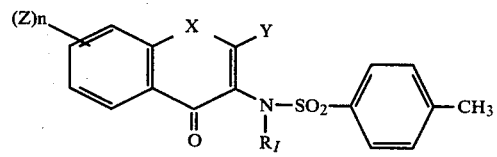

in accordance with the method described in Houben Weyl, Methoden der Organischen Chemie (Methods of Organic Chemistry), Volume 9, page 624.

c. The action of a strong acid on the compound resulting from the preceding stage, in accordance with the method described in Houben Weyl, Methoden der Organischen Chemie (Methods of Organic Chemistry), Volume 11/I, page 941.

The examples below illustrate the preparation of the compounds according to the invention and also their herbicidal properties.

EXAMPLE I

Preparation of 3-(3,3-dimethylureido)-chromone (compound 1) in accordance with process A 3-Aminochromone (14.5 g) is introduced into a solution (150 ml) of phosgene in toluene (2 mols/liter) and the mixture is heated to the reflux temperature in a round-bottomed flask equipped with a solid carbon dioxide condenser. The solid carbon dioxide condenser is replaced by a water condenser in order to complete the degassing. The mixture is left to return to ambient temperature and filtered on a glass frit. After washing with toluene (100 ml) and drying in vacuo, 3-isocyanatochromone (13 g) of m.p. 130° C. is obtained, this being a yield of 77.4%.

A solution of anhydrous dimethylamine (7.5 g) in dry toluene (100 ml) is added rapidly to a solution of 3-isocyanatochromone (13 g) in toluene (50 ml). The temperature of the reaction mixture rapidly rises from 20° to 47° C. and crystallization then takes place. The mixture is stirred for a further 20 minutes until the temperature of the reaction medium drops to about 25° C. After filtration, recrystallization from isopropyl ether (1,000 ml) and drying, 3-(3,3-dimethylureido)-chromone (5.4 g), which melts at 148° C., is obtained.

| | Percentage analysis | |
|---|---|---|
| | calculated % | found % |
| C | 62.06 | 62.10 |
| H | 5.21 | 5.25 |
| N | 12.06 | 11.95 |

The starting 3-aminochromone, which melts at 124° C., was obtained by reducing 3-nitrochromone with sodium hydrosulphite in an aqueous medium, in accordance with the method described in Tetrahedron Letters, No. 9, pages 719–20, 1976 (process 1).

3-Nitrochromone is prepared, in accordance with the method described in this article, from 2′-hydroxy-2-nitroacetophenone.

EXAMPLE II

The following compounds 2 to 19 were prepared from the appropriate starting materials by following the process described in Example 1. The results obtained are included in the table below, in which the figures shown in brackets in column Z indicate, in the case where n is different from O, the position of the substituent or substituents Z on the (thio)-chromone nucleus. In the case where n is equal to O, no indication is shown in this column Z.

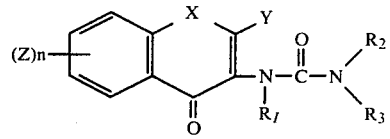

| Compound No. | X | Y | Z | $R_1$ | $R_2$ | $R_3$ | Yield % | M.p. °C. | | Percentage analysis | |
|---|---|---|---|---|---|---|---|---|---|---|---|
| | | | | | | | | | | Calculated % | Found % |
| 2 | O | H | Cl(6) | H | $CH_3$ | $CH_3$ | 88 | 211 | N | 10.50 | 10.20 |
| | | | | | | | | | Cl | 13.29 | 13.47 |
| 3 | O | H | $CH_3O$(7) | H | $CH_3$ | $CH_3$ | 61 | 200 | N | 10.68 | 10.62 |
| 4 | O | H | $(CH_3)_3C$(6) | H | $CH_3$ | $CH_3$ | 62 | 144 | N | 9.71 | 9.52 |
| | | | | | | | | | C | 66.65 | 66.40 |
| | | | | | | | | | H | 6.99 | 6.90 |
| | | | | | | | | | O | 16.65 | 16.67 |
| 5 | O | H | | H | —$(CH_2)_5$— | | 77.5 | 97 | N | 10.29 | 10.23 |
| | | | | | | | | | C | 66.16 | 65.70 |
| | | | | | | | | | H | 5.92 | 6.05 |
| | | | | | | | | | O | 17.63 | 17.25 |
| 6 | O | H | Cl(6)Cl(8) | H | $CH_3$ | $CH_3$ | 60 | 200 | N | 9.30 | 8.90 |
| | | | | | | | | | Cl | 23.55 | 23.90 |
| 7 | O | H | $CH_3$(6) | H | $CH_3$ | $OCH_3$ | 52 | 143 | N | 10.68 | 10.80 |
| 8 | O | H | $CH_3$(6) | H | $CH_3$ | $CH_3$ | 55 | 170 | N | 11.37 | 11.45 |
| 9 | O | H | $CH_3$(6) | H | —$(CH_2)_5$— | | 43 | 135 | N | 9.79 | 9.87 |
| 10 | O | H | $CH_3$(6) | H | $(CH_2)_2$–O–$(CH_2)_2$ | | 35 | 189 | N | 9.71 | 9.82 |
| 11 | O | H | | H | $C_2H_5$ | $C_2H_5$ | 52 | 70 | N | 10.76 | 10.45 |
| 12 | O | H | | H | $CH_3$ | $C_2H_5$ | 44.9 | 106 | N | 11.38 | 11.0 |

The 3-aminochromones used as the starting materials for the preparation of compounds 2 to 12 were prepared in accordance with process 1 described above.

EXAMPLE III

Preparation of 3-(3-methylureido)-chromone (compound 13) in accordance with process B Methyl isocyanate (4.2 g) is added to a suspension of 3-aminochromone (12 g) in anhydrous toluene (80 ml). The temperature of the reaction medium rises slowly from 20° C. to about 32° C. After 12 hours, the crystalline precipitate is filtered off and washed with acetonitrile (2×30 ml). After recrystallization from dimethylformamide (76 ml) at 100° C., filtering and drying under reduced pressure, 3-(3-methylureido)-chromone (8.5 g), which melts at 254° C., is obtained with a yield of 52.7%.

| | Percentage analysis | |
|---|---|---|
| | calculated % | found % |
| C | 60.55 | 60.10 |
| H | 4.62 | 4.25 |
| O | 21.99 | 22.70 |
| N | 12.84 | 12.95 |

The starting 3-aminochromone was prepared in accordance with process 1 described above.

EXAMPLE IV:

Compounds Nos. 14 to 21

The following compounds were prepared from the appropriate starting materials by following the procedure described in Example III.

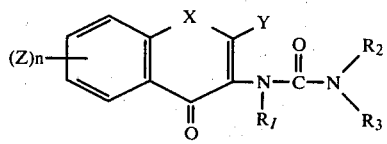

| Compound No. | X | Y | Z | R₁ | R₂ | R₃ | Yield % | M.p. °C. | Percentage Analysis | calculated % | found % |
|---|---|---|---|---|---|---|---|---|---|---|---|
| 14 | O | CH₃ | | H | H | CH₃ | 59.5 | 218 | C | 62.06 | 62.30 |
| | | | | | | | | | H | 5.21 | 5.35 |
| | | | | | | | | | O | 20.67 | 20.25 |
| | | | | | | | | | N | 12.06 | 11.95 |
| 15 | S | H | | H | H | CH₃ | 40.6 | 230 | N | 11.96 | 11.30 |
| | | | | | | | | | S | 13.69 | 13.45 |
| 16 | S | H | Cl (6) | H | H | CH₃ | 38.6 | 361 | N | 10.42 | 10.30 |
| | | | | | | | | | Cl | 13.19 | 13.10 |
| | | | | | | | | | S | 11.93 | 11.90 |
| 17 | S | H | CH₃ (6) | H | H | CH₃ | 77 | 270 | N | 11.28 | 10.50 |
| | | | | | | | | | S | 12.91 | 12.85 |
| 18 | S | H | CH₃ (6) | H | H | C₂H₅ | 46 | 202 | N | 10.68 | 10.20 |
| | | | | | | | | | S | 12.22 | 12.25 |
| 19 | S | H | | CH₃ | H | CH₃ | 35 | 232 | N | 11.28 | 11.25 |
| | | | | | | | | | S | 12.91 | 12.50 |
| 20 | S | H | | H | (CH₂)₂—CH₃ | H | 61.5 | 190 | N | 10.68 | 10.37 |
| | | | | | | | | | S | 12.22 | 12.48 |
| 21 | S | H | | H | —CH—(CH₃)₂ | H | 30 | 136 | N | 10.68 | 10.10 |
| | | | | | | | | | S | 12.22 | 12.50 |

The 3-amino-(thio)-chromones used as the starting materials were prepared in accordance with process 1, in the case of compound 14, and in accordance with process 2, in the case of compounds 15-18.

The 3-(methylamino)-thiochromone used as the starting material for the preparation of compound 19 was prepared in accordance with process 5 described above.

In order to do this, 3-aminothiochromone (7.4 g) is suspended in anhydrous pyridine (25 ml), the mixture is cooled to about 10° C. and para-toluenesulphonyl chloride (8.6 g) is then added, whist stirring. After dilution with distilled water (100 ml), precipitation, filtration, washing with ethanol and drying, 3-(p-toluenesulphonylamino)-thiochromone (13 g), which melts at 212° C., is obtained.

The product obtained above (12.9 g), methyl iodide (7.1 g) and anhydrous potassium carbonate (6.9 g) are introduced into acetonitrile (125 ml) and the mixture is heated under reflux for 5 hours. After cooling to ambient temperature, the precipitate formed is filtered off on a glass frit, washed with acetonitrile (50 ml), concentrated in vacuo and then taken up in distilled water (100 ml).

After decantation, the residue is triturated with a 20/80 mixture (50 ml) of diethyl ether and petroleum ether. The product crystallizes and is washed with ethanol (3×5 ml) and then dried. 3-[(N-p-Toluenesulphonyl-N-methyl)amino]-thiochromone (12.7 g), which melts at 102° C., is thus obtained.

The product (12.7 g) resulting from the preceding operation is then introduced into a mixture of acetic acid (40 ml) and sulphuric acid of density 1.83 (13 ml) and the mixture is heated for 3 hours at 85° C.

After cooling to ambient temperature, the mixture is poured onto crushed ice and then diluted with water (100 ml) and neutralised with an excess of potassium bicarbonate.

The aqueous phase is extracted with diethyl ether (2×500 ml) and decanted.

The extracts are then dried and filtered and the crystalline residue is taken up in isopropyl ether (2×20 ml).

After filtration and drying, 3-(methylamino)-thiochromone (5.3 g), which melts at 134° C., is thus obtained.

EXAMPLE V

Preparation of 3-(1,3,3-trimethylureido)-6-methylchromone (compound 22) in accordance with process C Triethylamine (4.15 ml) is added, without exceeding 5° C., to a solution, cooled to 5° C., of phosgene (2.3 g) in dry toluene. The appearance of a crystalline precipitate is noted. A solution of 3-methylamino-6-methylchromone (5.6 g) in methylene chloride (20 ml) is added gradually, whilst keeping the temperature in the region of 5° C. The addition is completed in about 20 minutes. The reaction medium is stirred for a further 30 minutes, whilst keeping the temperature at between 0° and 5° C. A solution of dimethylamine (2.7 g) in dry toluene (41.5 ml) is then added, whilst remaining within the same temperature limits. The mixture is stirred for a further 1 hour at between 0° and 5° C. and then for 1 hour at a temperature of about 20° C.

The reaction medium is diluted with methylene chloride (100 ml) and then washed with water (25 ml).

The decanted organic phase is dried over anhydrous sodium sulphate. After evaporating off the solvent under reduced pressure, the residue (weighing 6.5 g) is chromatographed on a column of silica (180 g), using ethyl acetate as the eluting solvent.

An oil (4.2 g) is thus obtained which crystallizes on trituration with diethyl ether (10 cc). After drying the crystals, 3-(1,3,3-trimethylureido)-6-methylchromone (2.4 g), which melts at 104°, is thus obtained.

Yield: 31%.

| | Percentage analysis | |
|---|---|---|
| | calculated % | found % |
| N | 10.76 | 10.72 |

The starting 3-methylamino-6-methylchromone, which melts at 118°–120° C., was prepared in accordance with process 5 described above.

EXAMPLE VI

Preparation of 3-(3,3-dimethylureido)thiochromone (compound 23) in accordance with process A A suspension of 3-aminothiochromone (9.3 g) in an approximately 2 M solution (129 ml) of phosgene in toluene is heated gradually, under a solid carbon dioxide reflux condenser, until the evolution of gas ceases. This operation requires prolonged heating (12 hours). The excess phosgene is then driven off by heating under reflux (water condenser). After cooling, the yellow-greenish precipitate is filtered off and washed with methylene chloride (2×50 ml).

After drying, 2-oxo-2,3-dihydro-benzothiopyrano[3,4d]oxazol-5-ium chloride (10.0 g) of the formula:

medium then crystallizes on concentration (to 100 ml). The precipitate is filtered off and the mother liquors are re-concentrated (to 50 ml); a second crop of crystals is thus obtained which is combined with the first.

After drying, 3-(3,3-dimethylureido)-thiochromone (5.8 g), which melts at 108° and again at 128° C., is obtained.

Yield: 58.5%.

| | Percentage analysis | |
|---|---|---|
| | calculated % | found % |
| N | 11.28 | 10.95 |
| S | 12.91 | 12.95 |

EXAMPLE VII

Compounds Nos. 24–33

The following compounds were prepared from the appropriate starting materials by operating in accordance with conditions indicated in Example VI:

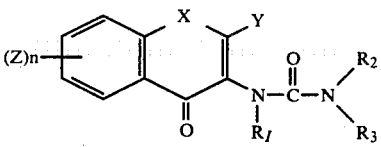

| Compound No. | X | Y | Z | $R_1$ | $R_2$ | $R_3$ | Yield | M.p. °C. | | Percentage analysis calculated % | found % |
|---|---|---|---|---|---|---|---|---|---|---|---|
| 24 | S | H | | H | H | $C_2H_5$ | 57.6 | 200 | N | 11.28 | 11.15 |
| | | | | | | | | | S | 12.91 | 13.0 |
| 25 | S | H | | H | H | $C(CH_3)_3$ | 92.3 | 122 | N | 10.14 | 9.80 |
| | | | | | | | | | S | 11.60 | 11.90 |
| 26 | S | H | $CH_3$ (6) | H | $CH_3$ | $CH_3$ | 52.8 | 160 | C | 59.52 | 59.0 |
| | | | | | | | | | N | 10.68 | 10.55 |
| | | | | | | | | | S | 12.22 | 12.17 |
| 27 | S | H | | H | $C_2H_5$ | $C_2H_5$ | 61.8% | 61 | N | 10.14 | 10.05 |
| | | | | | | | | | S | 11.60 | 11.90 |
| 28 | S | H | | H | $CH_3$ | $(CH_2)_3CH_3$ | 62.1% | 58 | N | 9.65 | 9.80 |
| | | | | | | | | | S | 11.04 | 11.20 |
| 29 | S | H | | H | $CH_3$ | $(CH_2)_2CH_3$ | 79.0 | 88 | N | 10.14 | 9.82 |
| | | | | | | | | | S | 11.60 | 11.49 |
| 30 | S | H | | H | $CH_3$ | $CH(CH_3)_2$ | 56.0 | 108 | N | 10.14 | 10.0 |
| | | | | | | | | | S | 11.60 | 11.60 |
| 31 | S | H | | H | $C_2H_5$ | $(CH_2)_2CH_3$ | 62.0 | 58 | N | 9.65 | 9.67 |
| | | | | | | | | | S | 11.04 | 11.05 |
| 32 | S | H | $(CH_3)_3C$ (6) | H | $CH_3$ | $CH_3$ | 33.0 | 142 | N | 9.20 | 9.07 |
| | | | | | | | | | S | 10.53 | 10.50 |
| 33 | S | H | $(CH_3)_3C$ (6) | H | $C_2H_5$ | $C_2H_5$ | 55.0 | 91 | N | 8.42 | 8.27 |
| | | | | | | | | | S | 9.64 | 9.47 |

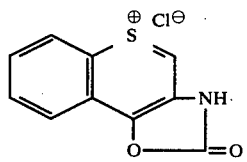

is thus obtained.

Yield 83.6%. M.p. about 160° C.

A solution of anhydrous dimethylamine (2.25 g) in dry toluene (41 ml) is added dropwise to a suspension of the product obtained above (9 g) in dry toluene (50 ml). The temperature of the medium rises gradually to 35° by the end of the addition. The suspension is stirred for 2 hours and the solvent is removed under reduced pressure. A residue (weighing 9 g) is obtained; it is taken up in ethyl acetate (1 liter), whilst stirring. After removal of a small amount of insoluble material by filtration, the solution is decolorized with absorbent charcoal and the The substituted 3-aminothiochromones used as the starting materials for the preparation of compounds nos. 24 to 31 were prepared in accordance with process 2.

3-Amino-6-tert.-butyl-thiochromone, which was the starting material for the preparation of compounds nos. 32 and 33, was prepared in accordance with process 3 by operating under the following conditions:

A suspension of 3-acetamido-6-tert.-butyl-thiochroman-4-one (44.6 g) and triphenylmethanol (46.8 g) in trifluoroacetic acid (40 ml) is heated gradually to 100° C., whilst stirring, and then kept at this temperature for 2 and a half hours. After cooling, the reaction medium crystallizes. It is taken up in methylene chloride (900 ml) and treated with an aqueous solution of potassium bicarbonate until the evolution of $CO_2$ ceases.

After drying, the methylene chloride solution is chromatographed on a silica column. 3-Acetamido-6-tert.- butyl-thiochromone (31.5 g), which melts at 215° C., is thus obtained.

A solution of 3-acetamido-6-tert.-butyl-thiochromone (31 g) in a 2 N solution (350 ml) of hydrochloric acid in methanol is heated gradually to the reflux temperature and kept at this temperature (70° C.) for 2 hours. After cooling, the reaction medium is poured into an excess of a 10% strength aqueous solution of potassium bicarbonate. A yellow solid precipitates which is filtered off, washed with water and dried. 3-Amino-6-tert.-butyl-thiochromone (26.2 g), which melts at 168° C., is thus obtained.

The 3-acetamido-6-tert.-butyl-thiochroman-4-one was prepared in accordance with the method described in Eur. J. Med. Chem. Chim. Ther., 11 (2), pages 145–51, 1976, in the case of 3-acetamidochroman-4-one.

EXAMPLE VIII

Herbicidal activity in a greenhouse, in pre-emergence and post-emergence testing.

A solution or dispersion of the material to be tested, which has the following composition, is prepared:
material to be tested: 400 mg
polyoxyethylene-sorbitan monooleate: 50 mg
acetone: 5 ml
distilled water containing 1 part per 1,000 of a product resulting from the condensation of 10 mols of ethylene oxide with 1 mol of octylphenol: q.s.p. 40 mol The solution or dispersion thus obtained is then diluted with water in order to obtain the desired dose.

The herbicidal activity of the products of the general formula I is demonstrated in the following manner:

Seeds of the following various species: wheat (Triticum sativum), lentil (Lens culinaris), radish (Raphanus sativus), beet (Beta vulgaris) and slender foxtail (Alopecurus agrestis), are sown in plastic pots (180 ml capacity) containing, to a height of 6 cm, a mixture composed of ⅓ of clean earth, ⅓ of vegetable mould and ⅓ of river sand, at the rate of about 30 seeds per pot.

For each dose of active material to be tested, two pots are used in the case of wheat and four pots are used for each of the other species.

In the case of a pre-emergence treatment, the treatment is carried out by spraying the solution or dispersion at the desired dose onto the surface of the earth, each pot receiving 1 ml of the solution or suspension. The seeded surface is allowed to dry and covered to a depth of 1 cm with the same earth mixture.

The pots are watered twice a day by sprinkling and are kept in a greenhouse (temperature 22°–24° C., relative humidity 70 to 80%) under artificial light which provides 5,000 to 6,000 Lux at the level of the plants for 17 hours per day.

In the case of a post-emergence treatment, the sowing is carried out in a greenhouse one week before the start of the experiment, so that the small plants are at the following stage at the time of treatment:
wheat and foxtail: 3 leaves
lentil: 3 leaves
beet and radish: 2 well-developed cotyledon leaves.

The treatment is carried out by spraying 1 ml, per pot, of the solution or suspension at the desired dose. The small plants are allowed to dry and the earth mixture is moistened by placing the base of the pots in a tray containing water. The pots are kept in a greenhouse under the same conditions as for the pre-emergence treatment. In both cases, the doses of active material applied are 1 and 10 kg/hectare.

Three weeks after the treatment, the number of small plants in each pot is counted and compared with the results obtained in the case of control pots which contain the same crops but have been treated with distilled water, and the results are expressed as a percentage, relative to the control plants.

A percentage equal to 100% indicates that there has been no destruction of the plant species in question. A percentage of 0% indicates that there has been complete destruction of the plant species in question.

The results observed are indicated in the table below according to the following scale:

| Percentage relative to the control plants | Corresponding figure of merit |
| --- | --- |
| 0 to 9% of the control plants | 0 complete herbicidal activity |
| 10 to 19% | 1 |
| 20 to 39% | 2 |
| 40 to 59% | 3 |
| 60 to 79% | 4 |
| 80 to 100% | 5 zero herbicidal activity |

| Compound No. | Dose kg/hectare | PRE-EMERGENCE | | | | | POST-EMERGENCE | | | | |
| --- | --- | --- | --- | --- | --- | --- | --- | --- | --- | --- | --- |
| | | wheat | lentil | radish | beet | foxtail | wheat | lentil | radish | beet | foxtail |
| 1 | 1 | 5 | 5 | 2 | 3 | 4 | 5 | 5 | 2 | 0 | 5 |
| | 10 | 5 | 5 | 0 | 0 | 2 | 0 | 0 | 0 | 0 | 0 |
| 2 | 1 | 5 | 5 | 1 | 0 | 2 | 5 | 4 | 2 | 2 | 5 |
| | 10 | 5 | 4 | 0 | 0 | 2 | 4 | 0 | 0 | 0 | 3 |
| 3 | 10 | 5 | 5 | 5 | 2 | 2 | 5 | 5 | 5 | 5 | 5 |
| 4 | 1 | 5 | 5 | 1 | 2 | 2 | 5 | 2 | 2 | 1 | 3 |
| | 10 | 5 | 5 | 0 | 0 | 2 | 5 | 2 | 0 | 0 | 2 |
| 6 | 10 | 5 | 5 | 5 | 5 | 5 | 2 | 5 | 4 | 4 | 3 |
| 7 | 1 | 5 | 5 | 5 | 5 | 5 | 5 | 5 | 5 | 0 | 5 |
| | 10 | 5 | 5 | 4 | 0 | 3 | 5 | 5 | 0 | 0 | 5 |
| 8 | 1 | 5 | 5 | 5 | 0 | 3 | 5 | 5 | 1 | 0 | 5 |
| | 10 | 3 | 4 | 0 | 0 | 2 | 5 | 5 | 0 | 0 | 4 |
| 9 | 1 | 5 | 5 | 5 | 5 | 5 | 5 | 5 | 4 | 0 | 5 |
| | 10 | 5 | 5 | 5 | 5 | 5 | 5 | 5 | 0 | 0 | 5 |
| 10 | 1 | 5 | 5 | 5 | 5 | 5 | 5 | 5 | 0 | 0 | 5 |

*-continued*

| Compound | Dose | | | | | | | | | | |
|---|---|---|---|---|---|---|---|---|---|---|---|
| 11 | 10 | 5 | 5 | 5 | 5 | 5 | 5 | 5 | 0 | 0 | 5 |
|    | 1  | 5 | 5 | 5 | 0 | 2 | 5 | 5 | 2 | 3 | 4 |
| 12 | 10 | 3 | 0 | 0 | 0 | 2 | 3 | 0 | 0 | 0 | 2 |
|    | 1  | 5 | 5 | 2 | 0 | 4 | 4 | 3 | 0 | 2 | 2 |
| 13 | 10 | 5 | 4 | 0 | 0 | 1 | 3 | 1 | 0 | 0 | 0 |
|    | 1  | 3 | 5 | 0 | 0 | 1 | 5 | 2 | 0 | 2 | 4 |
| 15 | 10 | 2 | 2 | 0 | 0 | 1 | 3 | 1 | 0 | 0 | 1 |
|    | 1  | 4 | 5 | 4 | 3 | 4 | 3 | 4 | 0 | 1 | 0 |
| 16 | 10 | 2 | 5 | 0 | 0 | 2 | 3 | 4 | 0 | 0 | 0 |
|    | 10 | 5 | 5 | 5 | 5 | 5 | 5 | 5 | 2 | 0 | 5 |
| 18 | 10 | 5 | 5 | 4 | 0 | 2 | 5 | 2 | 0 | 0 | 2 |
| 19 | 10 | 5 | 5 | 5 | 5 | 5 | 5 | 5 | 2 | 0 | 5 |
| 21 | 1  | 5 | 5 | 3 | 2 | 4 | 5 | 5 | 0 | 1 | 4 |
|    | 10 | 4 | 4 | 2 | 0 | 2 | 3 | 2 | 0 | 0 | 0 |
| 23 | 1  | 3 | 0 | 0 | 0 | 2 | 3 | 0 | 0 | 0 | 3 |
|    | 10 | 0 | 0 | 0 | 0 | 0 | 3 | 0 | 0 | 0 | 0 |
| 24 | 1  | 5 | 5 | 5 | 3 | 4 | 5 | 4 | 4 | 0 | 4 |
|    | 10 | 4 | 5 | 0 | 0 | 2 | 5 | 2 | 0 | 0 | 0 |
| 25 | 1  | 5 | 5 | 5 | 5 | 5 | 5 | 4 | 4 | 3 | 4 |
|    | 10 | 3 | 5 | 2 | 3 | 5 | 5 | 0 | 0 | 0 | 1 |
| 26 | 1  | 3 | 4 | 5 | 0 | 1 | 5 | 4 | 1 | 0 | 2 |
|    | 10 | 2 | 2 | 0 | 0 | 0 | 5 | 4 | 0 | 0 | 0 |
| 27 | 1  | 5 | 5 | 5 | 2 | 3 | 3 | 1 | 0 | 2 | 1 |
|    | 10 | 3 | 5 | 0 | 0 | 2 | 2 | 0 | 0 | 0 | 0 |
| 28 | 1  | 5 | 5 | 5 | 5 | 5 | 4 | 4 | 0 | 3 | 5 |
|    | 10 | 5 | 5 | 0 | 5 | 2 | 3 | 0 | 0 | 2 | 3 |
| 29 | 1  | 5 | 5 | 5 | 5 | 5 | 4 | 5 | 0 | 2 | 5 |
|    | 10 | 5 | 5 | 0 | 0 | 4 | 3 | 0 | 0 | 0 | 2 |
| 30 | 1  | 5 | 5 | 5 | 5 | 5 | 5 | 5 | 0 | 2 | 4 |
|    | 10 | 5 | 5 | 0 | 0 | 4 | 2 | 1 | 0 | 0 | 0 |
| 32 | 1  | 5 | 5 | 5 | 5 | 5 | 5 | 5 | 0 | 0 | 5 |
|    | 10 | 5 | 5 | 5 | 5 | 5 | 4 | 4 | 0 | 0 | 4 |
| 33 | 1  | 5 | 5 | 5 | 5 | 5 | 5 | 5 | 1 | 0 | 5 |
|    | 10 | 5 | 5 | 5 | 5 | 5 | 5 | 4 | 0 | 0 | 5 |

EXAMPLE IX

Herbicidal activity and selectivity in a greenhouse, in pre-emergence testing

This experiment was carried out using a wettable powder having the following composition:
compound to be tested: 500 g
sodium alkylnaphthalenesulphonate: 30 g
sodium salt of a product resulting from the condensation of naphthalenesulphonic acid: 50 g
kaolinite: 420 g In this experiment, stainless steel pots, having a square shape (side length of 28.5 cm) and a depth of 9 cm, are used. These pots are filled to a height of 6 cm with a mixture composed of ⅓ of clean earth, ⅓ of vegetable mould and ⅓ of river sand.

Several species of cultivated and adventitious plants are sown at the rate of one row per plant species and three pots are used for each concentration of product.

An aqueous suspension of the composition described above is prepared and diluted with water in order to obtain the desired concentration.

The treatment is carried out by spraying the suspension of the material to be tested onto the surface of the earth, at the desired concentration, using a multiple spray jet driven by a reciprocating mechanism.

After treatment, the pots are kept in a greenhouse (22°–24° C., relative humidity 70 to 80%) under artificial light which provides 5,000 to 6,000 Lux at the level of the plants for 17 consecutive hours per day. The pots are watered daily by sprinkling.

34 days after the treatment, the number of small plants in each pot is counted and compared with the results obtained in the case of control pots which contain the same plant species but have been treated with distilled water, and the results are expressed according to the same formal figure of merit of Example VIII.

The figure 0 indicates complete herbicidal activity on the species in question and the figure 5 indicates the absence of herbicidal activity.

The results observed are indicated in the table below:

| Dose in kg/hectare | Compound No. 27 | | | Compound No. 23 | | | Compound No. 13 | | | Compound No. 11 |
|---|---|---|---|---|---|---|---|---|---|---|
|  | 1 | 2 | 4 | 1 | 2 | 4 | 1 | 2 | 4 | 4 |
| CROPS | | | | | | | | | | |
| Maize (*Zea mays*) | 5 | 5 | 5 | 5 | 4 | 4 | 5 | 3 | 2 | 5 |
| Cotton (*Gossypium hirsutum*) | 5 | 5 | 5 | 5 | 5 | 5 | 5 | 5 | 2 | 5 |
| Horse bean (*Vicia Fabia equina*) | — | 5 | 5 | 5 | 5 | 5 | 5 | 4 | 2 | 5 |
| Soya (*Glycine max*) | 5 | 5 | 5 | 5 | 4 | 0 | 4 | 0 | 0 | 4 |
| Sunflower (*Helianthus annus*) | — | 5 | 5 | 4 | 1 | 0 | 0 | 0 | 0 | 1 |
| Rice (*Oryza sativa*) | 5 | 3 | 2 | 5 | 4 | 2 | 3 | 3 | 2 | 5 |
| ADVENTITIOUS PLANTS | | | | | | | | | | |
| Crabgrass (*Digitaria sanguinalis*) | 0 | 0 | 0 | 0 | 0 | 0 | 0 | 0 | 0 | 0 |
| Panic grass (*Echinocrus-galli*) | 1 | 0 | 0 | 0 | 0 | 0 | 0 | 0 | 0 | 1 |
| Wild oat (*Avena fatua*) | 4 | 2 | 0 | 0 | 0 | 0 | 1 | 0 | 0 | 1 |
| Green panic grass (*Setaria viridis*) | 0 | 0 | 0 | 1 | 1 | 0 | 0 | 0 | 0 | 0 |
| Foxtail (*Alopecurus agrestis*) | 0 | 0 | 0 | 0 | 0 | 0 | 0 | 0 | 0 | 1 |
| Goosefoot | | | | | | | | | | |

-continued

| Dose in kg/hectare | Compound No. 27 | | | Compound No. 23 | | | Compound No. 13 | | | Compound No. 11 |
|---|---|---|---|---|---|---|---|---|---|---|
|  | 1 | 2 | 4 | 1 | 2 | 4 | 1 | 2 | 4 | 4 |
| (*Chenopodium sp*) Chickweed | 0 | 0 | 0 | 0 | 0 | 0 | 0 | 0 | 0 | 1 |
| (*Stellaria media*) | 0 | 0 | 0 | 0 | 0 | 0 | 0 | 0 | 0 | 0 |

These results show the good herbicidal activity of compounds nos. 11, 13, 23 and 27, with respect to the adventitious plants tested, and also their selectivity in pre-emergence treatment, with respect to the main crops tested.

Particularly valuable results have been obtained in the case of 3-(3,3-diethylureido)-thiochromone (compound no. 27) which exhibits an excellent herbicidal activity against most of the adventitious plants tested, as from a dose of 1 kg/hectare, and which is well tolerated by crops such as maize, cotton, soya, sunflower and horse bean at a dose of 4 kg/hectare.

The compounds according to the invention can be used for selectively combating weeds in crops such as maize, soya, cotton, sunflower, rice and horse bean, in the pre- or post-emergence treatment of the latter. The use dose can vary according to the compound employed and the crop in question, but it is generally between 0.5 and 4 kg/hectare.

For their use in practice, the compounds according to the invention are not generaly employed by themselves. Most frequently, they form part of compositions which generally comprise, in addition to the active material according to the invention, a carrier and/or a surface-active agent. The proportion of active material in these compositions can vary within wide limits, in practice, this proportion of active material is preferably between 5 and 95% by weight.

The term "carrier", for the purpose of the present description, denotes an organic or inorganic, natural or synthetic material with which the active material is combined in order to facilitate its application to the plant, to seeds or to the soil, or in order to facilitate its transportation or handling. The carrier can be solid (clays, natural or synthetic silicates, resins, waxes, solid fertilisers or the like) or fluid (water, alcohols, ketones, petroleum fractions, chlorohydrocarbons or liquefied gases).

The surface-active agent can be an emulsifier, dispersing agent or wetting agent, which can be ionic or nonionic. Examples which may be mentioned are salts of polyacrylic acids and of ligninsulphonic acids, and products resulting from the condensation of ethylene oxide with fatty alcohols, fatty acids or fatty amines.

The compositions according to the invention can be prepared in the form of wettable powders, dusting powders, solutions, emulsifiable concentrates, emulsions, suspension concentrates and aerosols.

The wettable powders according to the invention can be prepared e.g. by grinding the active material with the solid carrier, so that they contain from 20 to 95% by weight of the active material, and they usually contain from 3 to 10% by weight of a dispersing agent and, where necessary, from 0 to 10% by weight of one or more stabilisers and/or other additives such as penetrating agents, adhesives or anti-caking agents, dyestuffs and the like.

By way of example, the composition of a wettable powder is given, the percentages being expressed by weight:
active material (compound no. 27): 50%
calcium lignosufonate (deflocculant): 5% isopropyl naphthalenesulphonate
(wetting agent): 1%
anti-caking silica: 5%
kaolin filter: 39%

The dusting powders are usually prepared in the form of a dust concentrate having a composition which is similar to that of a wettable powder but without the dispersing agent, and they can be diluted on site with a complementary amount of fluid carrier so as to obtain a composition which can conveniently coat the grains to be treated and usually contains from 0.5 to 10% by weight of active material.

By way of example, the composition of a dusting powder is given, the percentages being expressed by weight.
active material: compound no. 27: 50%
anionic wetting agent: 1%
anti-caking silica: 6%
kaolin (filler): 43%

The emulsifiable concentrates which can be applied by spraying, after dilution with water, usually contain the active material in solution in a solvent and, in addition to the solvent and where necessary, a co-solvent, from 10 to 50% by weight/volume of active material and from 2 to 20% by weight/volume of suitable additives such as stabilizers, penetrating agents, corrosion inhibitors and dyestuffs and adhesives.

By way of example, the composition of an emulsifiable concentrate is given, the amounts being expressed in g/liter:
active material: compound no. 23: 125 g/liter
dodecyl benzenesulphonate: 24 g/liter
oxyethyleneated nonylphenol containing 10 molecules of ethylene oxide: 16 g/liter
cyclohexanone: 200 g/liter
aromatic solvent: q.s.p.    1 liter The suspension concentrates, which can also be applied by spraying, are prepared so as to obtain a stable fluid product which does not form a deposit, and they usually contain from 10 to 75% by weight of active material, from 0.5 to 15% by weight of surface-active agents, from 0.1 to 10% by weight of anti-sedimentation agents such as protective colloids and thixotropic agents, from 0 to 10% by weight of suitable additives such as anti-foam agents, corrosion inhibitors, stabilizers, penetrating agents and adhesives, and, as the carrier, water or an organic liquid in which the active material is essentially insoluble; certain solid organic materials or inorganic salts can be dissolved in the carrier to assist in preventing sedimentation or to act as anti-freeze agents for the water.

Aqueous dispersions and aqueous emulsions, for example compositions obtained by diluting a wettable powder or an emulsifable concentrate, according to the invention, with water, at the rate of 10 to 100 g of active material per hectoliter of water, fall within the general scope of the present invention. These emulsions can be of the water-in-oil or of the oil-in-water type and they can have a thick consistency such as that of a "mayonnaise".

The compositions according to the invention can contain other ingredients, e.g. protective colloids, adhesives or thickeners, thixotropic agents, stabilizers or sequestering agents, as well as other known active materials having pesticidal properties, in particular insecticidal or fungicidal properties.

I claim:

1. A 3-ureido-(thio)-chromone derivative of the formula

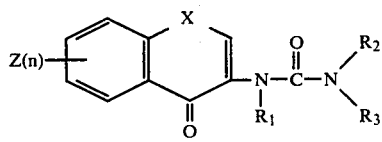

in which:

X represents an oxygen or sulphur atom, n is an integer which can be equal to 0 or 1, Z represents a halogen atom or an alkyl radical containing from 1 to 6 carbon atoms, $R_1$ represents a hydrogen atom or an alkyl radical containing 1 to 4 carbon atoms and $R_2$ and $R_3$, which are identical or different, each represent a hydrogen atom or an alkyl radical containing from 1 to 4 carbon atoms.

2. A compound according to claim 1 in which X is sulfur.

3. A compound according to claim 1 in which X is oxygen.

4. A compound according to claim 1 wherein $R_1$ is hydrogen.

5. A compound according to claim 1 wherein $R_1$ is hydrogen and $R_2$ and $R_3$ are each an alkyl radical containing 1–4 carbon atoms.

6. A compound according to claim 1 wherein $R_1$ and $R_2$ are each hydrogen and $R_3$ is an alkyl radical containing 1–4 carbon atoms.

7. A compound according to claim 1 of the formula:

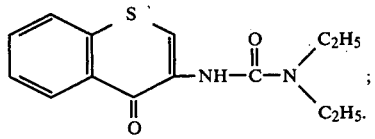

* * * * *